Figure 1:
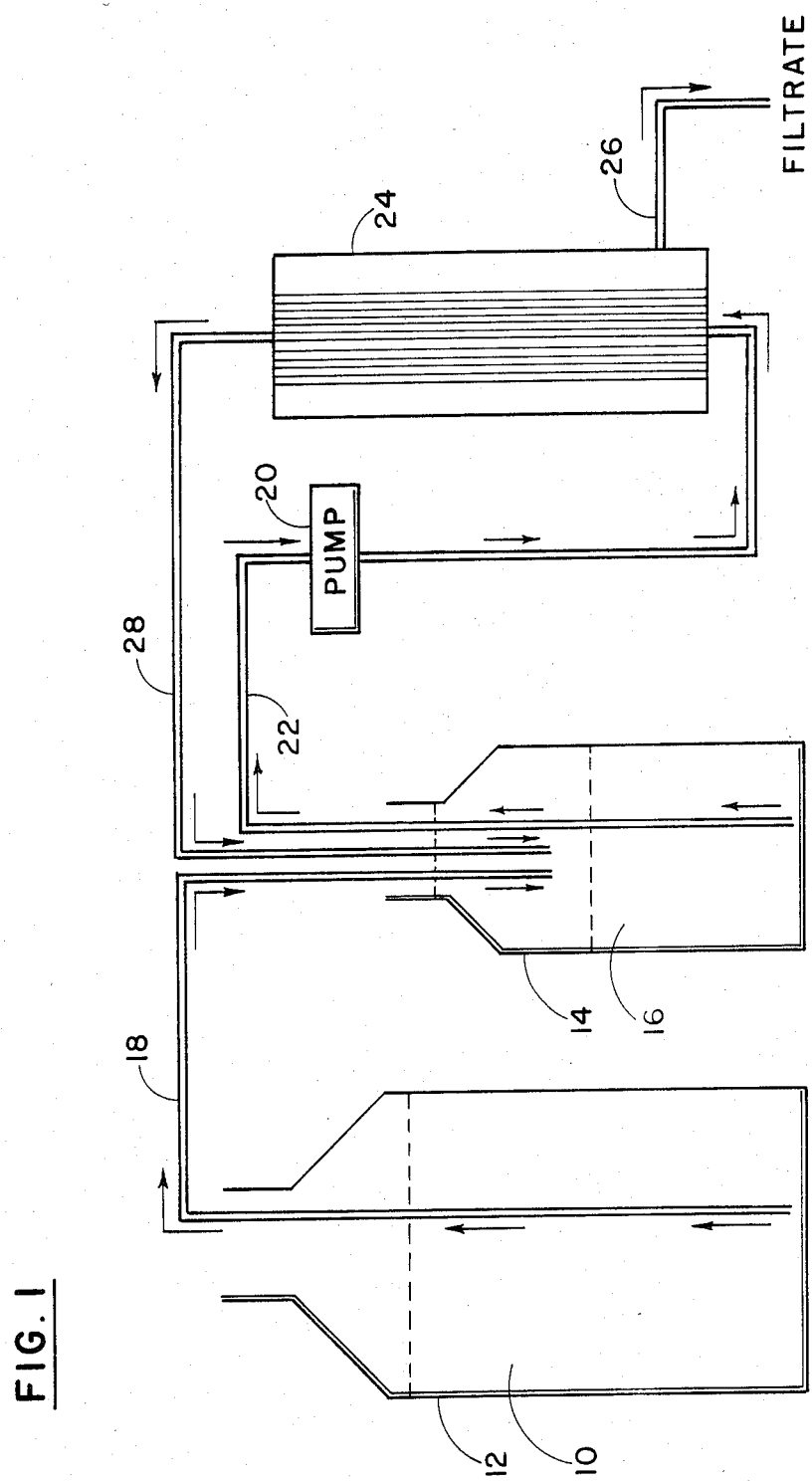

United States Patent [19]

Kothe et al.

[11] Patent Number: 4,526,715

[45] Date of Patent: Jul. 2, 1985

[54] METHOD OF PREPARING HIGHLY PURIFIED, STROMA-FREE, NON-HEPATITIC HUMAN AND ANIMAL HEMOGLOBIN SOLUTIONS

[75] Inventors: Norbert Kothe, Kronberg; Bertram Eichentopf, Bad Soden, both of Fed. Rep. of Germany

[73] Assignee: Biotest Pharma GmbH, Frankfurt, Fed. Rep. of Germany

[21] Appl. No.: 614,595

[22] Filed: May 29, 1984

[30] Foreign Application Priority Data

Mar. 31, 1984 [DE] Fed. Rep. of Germany ....... 3412144

[51] Int. Cl.$^3$ ............ A61K 35/18; A61K 37/02; C07G 7/00; C07C 103/52
[52] U.S. Cl. .................... 260/112 B; 260/112.5 R; 424/101; 514/2
[58] Field of Search .............. 260/112 B, 112.5; 424/101, 177

[56] References Cited

U.S. PATENT DOCUMENTS

| 3,864,478 | 2/1975 | Bonhard | 424/101 |
| 4,001,200 | 1/1977 | Bonsen et al. | 260/112 B X |
| 4,136,093 | 1/1979 | Bonhard et al. | 260/112 B X |
| 4,376,059 | 3/1983 | Davis et al. | 260/112 B X |
| 4,401,652 | 8/1983 | Simmonds et al. | 260/112 B X |
| 4,439,357 | 3/1984 | Bonhard et al. | 260/112 B |

OTHER PUBLICATIONS

F. DeVenuto et al., Characteristics of Stroma-Free Hemoglobin Prepared by Crystallization, Letterman Army Institute of Research, CA, 1976, pp. 509–516.

F. DeVenuto et al., Appraisal of Hemoglobin Solution as a Blood Substitute, Letterman Army Institute of Research, CA, (Surgery, Gynecology & Obstetrics-)–Sep. 1979, vol. 149, pp. 417–435.

Mario Feola et al., Development of a Bovine Stroma--Free Hemoglobin Solution as a Blood Substitute, Gynecology & Obstetrics, 11/83, vol. 157, No. 5, pp. 399–408.

*Primary Examiner*—Howard E. Schain
*Attorney, Agent, or Firm*—Sprung Horn Kramer & Woods

[57] ABSTRACT

To provide a method that allows the preparation, not only from human blood but also from animal blood and in quantities large enough for clinical applications, of highly purified hemoglobin solutions that can be employed for the treatment of humans and that are free of plasma proteins and residual stroma lipids (a) a starting material that contains erythrocytes is pumped over a filter unit that has a pore size between 0.1 and 1.2 $\mu$m in circulation against an isotonic washing solution, (b) the product of (a) is hemolyzed and pumped over an ultrafiltration unit that has a permeability of 80,000 to 100,000 D in circulation against water, and (c) the ultrafiltrate obtained in stage (b) is pumped and diafiltered over an ultrafiltration unit that has a permeability of 10,000 to 50,000 D in circulation against water, whereby concentration is conducted before and/or after diafiltration.

6 Claims, 2 Drawing Figures

4,526,715

METHOD OF PREPARING HIGHLY PURIFIED, STROMA-FREE, NON-HEPATITIC HUMAN AND ANIMAL HEMOGLOBIN SOLUTIONS

BACKGROUND OF THE INVENTION

The present invention relates to a method of preparing highly purified, stroma-free, non-hepatitic human and animal hemoglobin solutions.

Hemoglobin solutions have the capacity to transport oxygen in vivo independent of erythrocytes. For the compatibility of such solutions, however, it is necessary to remove as completely as possible the plasma and cell components (plasma proteins, stroma, etc.) of the blood from which the hemoglobin is to be released by hemolysis.

Various methods of preparing hemoglobin solutions are in use.

The first stage of all these methods consists of washing the erythrocytes to remove the plasma proteins. In most of the methods known up to now the erythrocytes are treated with isotonic electrolyte solutions and separated by centrifugation as described for example in German Pat. No. 2 248 475.

U.S. Pat. No. 4,439,357 describes a method that is also appropriate for large-scale preparation and involves sedimentation for the purpose of washing the erythrocytes.

The next step in all preparation methods is hemolysis of the erythrocytes followed by separating out of the stroma components, which can be done by filtration, centrifugation, recrystallization of the hemoglobin, or by a combination of these procedures (U.S. Pat. No. 4,439,357; De Venuto et al., "Appraisal of Hemoglobin Solution as a Blood Substitute, *Surgery, Gynecology & Obstetrics,* 149 [September 1979], 417-36; De Venute et al., "Characteristics of Stroma-free Hemoglobin Prepared by Crystallization," *J. Clin. Med,* March 1977, 509-16; Feola et al., "Development of a Bovine Stroma-free Hemoglobin Solution as a Blood Substitute," *Surgery, Gynecology & Obstetrics,* November 1983).

This maximally possible removal of the stroma is especially significant because residual stroma lipids can possibly affect blood clotting and provoke renal damage.

All of the methods of preparing hemoglobin solutions employed up to the present time, however, exhibit decisive drawbacks. Present procedures for washing the erythrocytes have led to products that still contain plasma proteins. Complete removal of the plasma proteins by repeated washing of the erythrocytes or recrystallization of the hemoglobin results in considerable losses of yield and is uneconomical on a large scale.

For this reason it has also been impossible by conventional methods to prepare hemoglobin solutions from animal blood for possible utilization in human medicine because the residual proteins in the solutions can lead to immune reactions when employed with humans.

SUMMARY OF THE INVENTION

The object of the present invention is to provide a method that allows the preparation, not only from human blood but also from animal blood and in quantities large enough for clinical applications, of highly purified hemoglobin solutions that can be employed for the treatment of humans and that are free of plasma proteins and residual stroma lipids.

This object is attained in accordance with the invention in that (a) a starting material that contains erythrocytes is pumped over a filter unit that is to be overflowed and that has a pore size between 0.1 and 1.2 $\mu$m in circulation against an isotonic washing solution, whereby used washing solution is continuously drawn off and replenished with fresh washing solution, (b) the accordingly washed and concentrated erythrocytes are harvested from the filter and hemolyzed in a way that is in itself known, the hemolysate is pumped at almost constant volume over an ultrafiltration unit that is to be overflowed and that has a permeability of 80,000 to 100,000 D in circulation against water, and (c) the dilute hemoglobin solution obtained in stage (b) as an ultrafiltrate is pumped at almost constant volume over an ultrafiltration unit that is to be overflowed and that has a permeability of 10,000 to 50,000 D in circulation against water and hence diafiltered, whereby pumping continues in circulation before and/or after diafiltration through the same ultrafiltration unit but without a countercurrent of water until the hemoglobin is concentrated to the desired level.

The combination of filtration with filter membranes of decreasing pore diameter in accordance with the invention makes it possible to free the erythrocytes of plasma proteins, to completely remove the erythrocyte covering membranes, and to purify the hemoglobin of undesirable companion substances.

Figure 2:
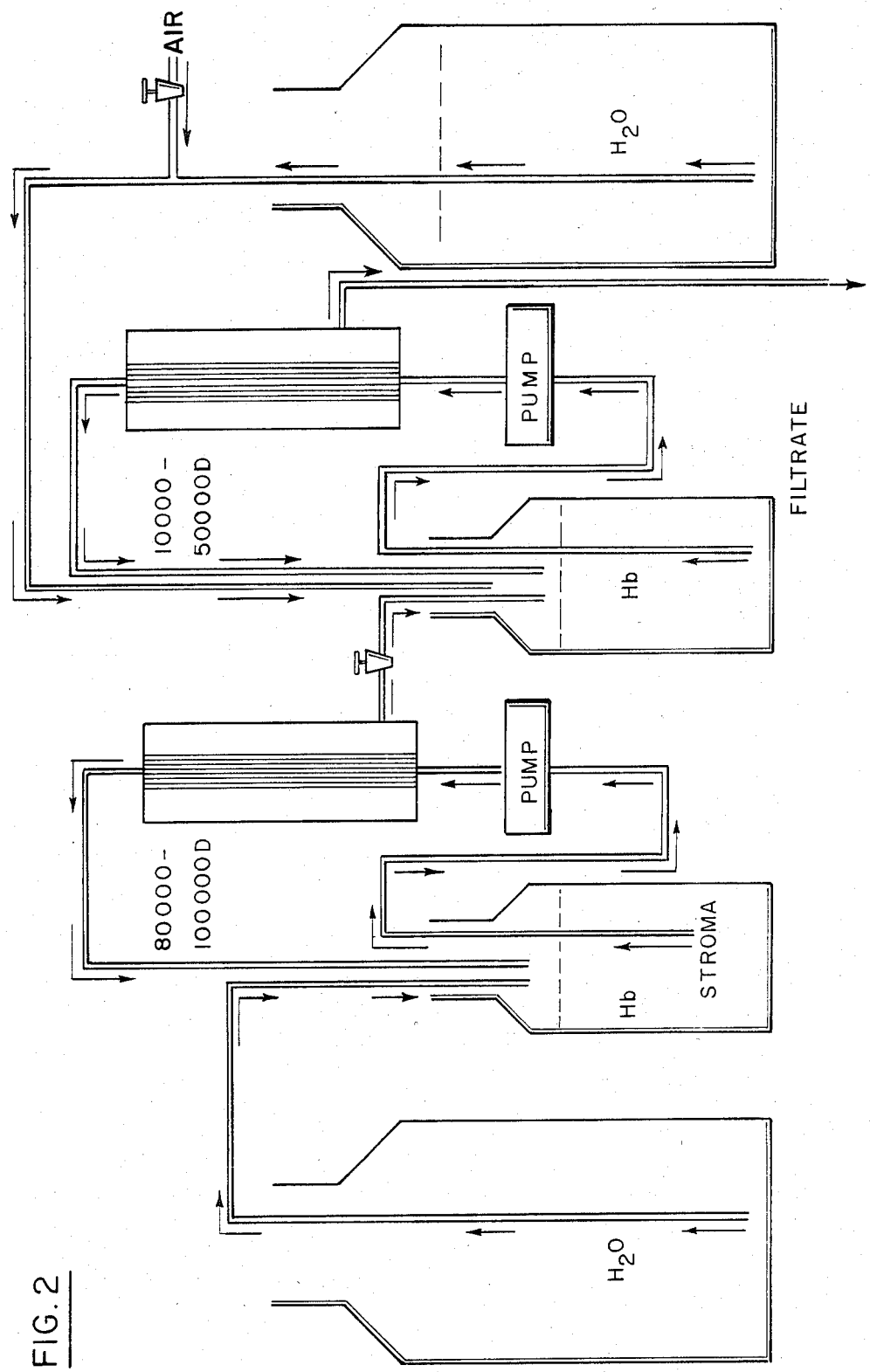

The invention will be further described with reference to the accompanying drawings wherein:

FIG. 1 is a schematic sketch of an apparatus for washing the erythrocytes in accordance with the invention; and FIG. 2 is a schematic sketch of an apparatus for separating the stroma in accordance with the invention.

Referring now more particularly to the drawing, in FIG. 1 an isotonic washing solution of electrolyte 10 is passed from a container 12 to a vessel 14 which contains erythrocytes 16, passing over a tube 18. A pump 20 withdraws solution from vessel 14 through tube 22 and delivers it to a membrane filter 24. Washing solution containing dissolved proteins is withdrawn from the filter at 26 while washing solution containing any erythrocytes is returned via tube 28 to the vessel 14. This circulation of isotonic solution through vessel 14 and filter 24 is continued as long as desired to arrive at a predetermined level of protein removal. Technical-grade pumps and technical-grade filtration modules of the type conventionally employed to recover lacquer pigments can be employed.

Erythrocytes will as is known undergo hemolysis very readily, and one skilled in the art constantly strives to wash them as gently as possible to prevent this from happening. Especially liable to hemolysis are old erythrocyte concentrates that have been stored for a long time.

It was accordingly completely surprising to discover that hemolysis hardly occurred when circulating with technical-grade pumps over technical-grade filter modules, which one skilled in the art would certainly not consider gentle treatment, and this was especially surprising in the case of outdated erythrocyte concentrates, e.g. as old as 12 weeks from the date of donation.

The method in accordance with the invention can accordingly be employed not only for fresh whole blood of animal or human provenance but also for outdated human-erythrocyte concentrates without the occurrence of significant hemolysis.

The first step in the method makes it possible to bring large quantities of washing solution into contact with erythrocytes in a short time and to remove them again from circulation to produce intense washing.

All isotonic electrolyte solutions or isotonic solutions of sugar or sugar alcohols are appropriate washing solutions. An isotonic NaCl solution is preferred.

Since any volume of erythrocytes can be washed by simply increasing the surface of the filter, the method is appropriate for the large-scale preparation of hemoglobin solutions.

The filter employed can contain either flat membranes or hollow-fiber membranes. Hollow-fiber membranes are preferred because they offer more surface in a smaller space than flat membranes.

The mean pore size of the filter membranes ranges from 0.1 to 1.2 $\mu$m. If the lower limit is exceeded, plasma proteins can be retained along with the erythrocytes, whereas, if the upper limit is exceeded, the rate of hemolysis will be drastically increased. Membranes with a mean pore size of 0.4 to 0.6 $\mu$m are preferred.

It is practical for the filtration pressure to range from 50 to 700 mbars.

Circulation washing is continued until no more plasma proteins are demonstrable.

Once the erythrocytes have been washed, hemolysis occurs as described by introducing the concentrated erythrocytes into 2 to 3 times their volume of water.

The second and third steps of the method, illustrated in FIG. 2, consist of separating the stroma from the hemoglobin. Immediately subsequent to hemolysis, the hemoglobin released from the erythrocyte is separated from the erythrocyte stroma in a second filtration stage. The hemolysate is accordingly intensively diafiltered against water, an ultrafiltration unit with a permeability of 80,000 to 100,000 D (flat membranes or hollow-fiber membranes, but preferably the latter) being employed.

This means that the hemolysate is pumped in circulation at almost constant volume over the ultrafiltration unit, whereby the hemoglobin appears with a molecular weight of 64,500 along with all companion substrates with a molecular weight of less than 80,000 to 100,000 D in the ultrafiltrate.

The advantage of this method is that almost all the hemoglobin can be harvested from the present hemolysate, in contrast to previous methods, in which a large part of the hemoglobin is thrown out with the erythrocyte stroma.

The dilute hemoglobin solution that occurs in this second filtration stage in the form of an ultrafiltrate is concentrated in a third filtration stage parallel to the second filtration. An ultrafiltration unit is employed again, but with a permeability of 10,000 to 50,000 D, retaining the hemoglobin as well as not only concentrating it but already partly freeing it of companion substances with molecular weights below the aforementioned permeability of the membrane employed. As soon as the hemoglobin has been concentrated to a desired level, it is again diafiltered against water to completely impoverish it of small-molecular companion substances.

Diafiltration can, however, be conducted at practically any point in the third filtration stage. Diafiltration can for example be carried out first, followed by concentration, or vice versa. If, however, the volume of the hemoglobin solution must not be too great nor the solution itself be too concentrated for purposes of diafiltration, it is practical to diafilter more or less in the middle of the third step, meaning that concentration to a specific level is carried out first, followed by diafiltration and then by final concentration to the desired level.

The filtration pressure in the second and third filtration stages is limited only by the maximal permissible pressure of the particular filter module employed. This is indicated on the module by the manufacturer.

The result is a highly purified hemoglobin of a desired concentration that can be processed by conventional methods into modified hemoglobin solutions like those described for example in German Pat. Nos. 2 449 252, 6 617 822, and 2 714 252, whereby the foregoing literature citations are intended to refer only to modification and not to purification.

The filtrations in all three stages are what are called tangential overflowing filtrations. The material to be filtered would clog up the pores very rapidly in conventional filtration.

Desalinated or distilled water is preferably employed.

Although the method of preparing hemoglobin solutions described in the article by Mario Feola et al. and previously cited herein involves two steps, in which the hemolysate is passed through filters with permeabilites of 100,000 and 30,000 D, the preliminary washing of the erythrocyte occurs conventionally in that method with an electrolyte solution, whereby the plasma protein is not completely separated. Furthermore, the ultrafiltrate from the last 30,000 D, filtration is dialyzed against an electrolyte, with the consequence that the resulting hemoglobin solution exhibits a high electrolyte content, which is a drawback in special applications like perfusion of the coronary vessels in open-heart (cardioplegia) operations. The method in accordance with the invention, in which diafiltration occurs against water in the second and third stages, results on the other hand in a practically electrolyte-free product.

Finally, filtration through a filter with a pore size of 0.5 $\mu$m occurs upstream of the two ultrafiltrations subsequent to hemolysis because one skilled in the art would have to have assumed that the filter would very rapidly become clogged when immediately filtering a hemolysate still containing coarse cell components through a 100,000-D filter.

It has, however, surprisingly been discovered that, when the hemolysate is pumped in circulation against water over a 100,000-D filter in accordance with the invention, the filter will not become clogged and an upstream hemolysate-filtration stage involving a coarser filter can be eliminated.

The advantages of the combined method in accordance with the invention consist on the one hand of technically simple realization plus a considerable saving of time and a higher yield of hemoglobin in comparison with previously described methods and on the other in that the high purity of the hemoglobin obtained creates a potential for the use of animal blood to prepare modified hemoglobin solutions for the therapy of humans. Furthermore, the product is practically free of electrolytes and the method leads to a drastic reduction of any virus or bacteria that may be present in the starting material, so that the chemical sterilization familiar from previous methods, with $\beta$-propiolactone for example (cf. German Pat. No. 2 248 475 & U.S. Pat. No. 4,439,357) can be eliminated. In special cases, however, $\beta$-propiolactone treatment can be carried out in conjunction with the method in accordance with the invention while the erythrocytes are being washed.

The invention will now be described with reference to the following examples.

EXAMPLE 1

5 l of fresh stabilized bovine blood was filtered over a blood filter into a 5-l vessel. The blood was pumped with a blood pump in circulation over two hollow-fiber filtration cartridges with pores 0.4 μm wide and a total surface of 1 m². The volume filtered out of circulation was continuously replaced with a 0.9% NaCl solution. To almost completely remove the plasma proteins, 50 l (10 times the initial volume) of NaCl solution were employed for washing. The mean filtration pressure was 266 mbar. Washing was terminated in 3 hours. The erythrocytes were subsequently concentrated. The erythrocyte concentrate was stirred into 5 l of distilled water, initiating hemolysis. To remove the stroma the hemolysate was pumped in circulation over 2 hollow-fiber cartridges (1.8 m²) with a permeability of 100,000 D. The hemoglobin (MG 64,500) passed through the membrane, whereas the stroma components and higher-molecular substances were retained. The circulation volume was maintained constant by continuously adding distilled water. About 95% of the total hemoglobin was contained in 30 l of ultrafiltrate. As soon a 5 l of ultrafiltrate had been obtained, the hemoglobin was again concentrated, the volume being maintained constant, in another circulation incorporating two hollow-fiber cartridges with a permeability of 10,000 D (1.8 m²). Upon termination of stroma separation and with a volume of 5 l containing 95% of the total hemoglobin, the material was diafiltered over the same ultrafiltration unit with a permeability of 10 000 D against 25 l of distilled water to remove the low-molecular components. In the last stage, the hemoglobin was concentrated to 22% in the same circulation, Finally, the solution was filter sterilized over a 0.2-μm filter.

Yield: 80%.

EXAMPLE 2

Complete removal of the plasma proteins from the hemoglobin solution was demonstrated by immune electrophoreses and in animal tests. Guinea pigs were immunized with a hemoglobin solution prepared as in Example 1 with the aid of Freund's adjuvant. No antibodies against human plasma proteins or against animal plasma proteins were demonstrable in the animals' plasma.

EXAMPLE 3

A drastic decrease in the number of pathogens present in the starting blood as a result of the method in accordance with the invention was also demonstrable in tests. When either $\Phi \times 174$ phages with a diameter of ca. 25 nm or κ phages with a diameter of 200 nm were added in a concentration of $10^7$/ml were added to the blood employed to prepare the hemoglobin solution, it could be demonstrated that washing the erythrocytes with 10 times the volume of washing solution in the first filtration stage resulted in an impoverishment of $10^3$ to $10^4$ phages.

In the next filtration stage, in which the freed hemoglobin was filtered out through an ultrafiltration membrane with a permeability of 100 000 D, another $10^3$/ml of phages were retained by the membrane, which their diameter prevented them from passing through. Hence the added phages were decreased by about $10^6$/ml to 10/ml. This sterilization effect is especially significant because transfusion blood tested in accordance with conventional blood-bank criteria can as before transmit hepatitis. As already stated previously herein, this made chemical sterilization necessary with previous methods. The new filtration method described herein makes it possible to eliminate chemical sterilization.

It will be understood that the specification and examples are illustrative but not limitative of the present invention and that other embodiments within the spirit and scope of the invention will suggest themselves to those skilled in the art.

We claim:

1. A method of preparing a highly purified, stroma-free, non-hepatitic human or animal hemoglobin solution, comprising
   (a) pumping a starting material that contains erythrocytes to overflow a filter unit that has a pore size between 0.1 and 1.2 μm in circulation against an isotonic washing solution, continuously drawing off used washing solution and replenishing it with fresh washing solution,
   (b) harvesting the washed and concentrated erythrocytes from the filter, hemolyzing the erythrocytes, pumping the hemolysate at almost constant volume to overflow an ultrafiltration unit that has a permeability of 80,000 to 100,000 D in circulation against water, and
   (c) pumping the dilute hemoglobin solution obtained in step (b) as an ultrafiltrate at almost constant volume to overflow an ultrafiltration unit that has a permeability of 10,000 to 50,000 D in circulation against water thereby to effect diafiltration, and continuing pumping in circulation before and/or after diafiltration through the same ultrafiltration unit but without a countercurrent of water until the hemoglobin is concentrated to a predetermined level.

2. A method according to claim 1 wherein in step (c) pumping in circulation until the hemoglobin is concentrated to the desired level is effected prior to diafiltering in circulation through the same ultrafiltration unit against water, and adjustment of the hemoglobin to the desired final concentration is thereafter effected.

3. A method according to claim 1, wherein step (a) is carried out at a filtration pressure of 50 to 700 mbar.

4. A method according to claim 1, wherein an isotonic NaCl solution is employed as the washing solution in step (a).

5. A method according to claim 1, wherein a filtration unit with a pore size of 0.4 to 0.6 μm is employed in step (a).

6. A method according to claim 1, wherein a hollow-fiber membrane is employed in all three steps as a filtration or ultrafiltration unit.

* * * * *